United States Patent [19]  
Cragoe, Jr. et al.

[11] 3,989,749  
[45] Nov. 2, 1976

[54] 11,12-SECOPROSTAGLANDINS

[75] Inventors: Edward J. Cragoe, Jr., Lansdale; James H. Jones, Blue Bell, both of Pa.

[73] Assignee: Merck & Co., Inc., Rahway, N.J.

[22] Filed: Jan. 27, 1975

[21] Appl. No.: 544,474

Related U.S. Application Data

[63] Continuation-in-part of Ser. No. 407,008, Oct. 17, 1973, abandoned.

[52] U.S. Cl. .................. 260/534 M; 260/247.1 R; 260/247.2 A; 260/268 R; 260/284; 260/286 R; 260/293.85; 260/293.86; 260/326 E; 260/326.5 S; 260/326.5 L; 260/326.8; 260/326.83; 260/326.85; 260/345.9; 260/429.9; 260/439 R; 260/448 R; 260/468 J; 260/481 R; 260/482 R; 260/484 A; 260/484 R; 260/488 R; 260/490; 260/501.11; 424/250; 424/267; 260/501.12; 424/274; 424/287; 260/514 J; 424/289; 424/295; 260/539 R; 424/311; 424/316; 260/552 R; 424/319; 260/553 R; 424/248

[51] Int. Cl.$^2$................ C07C 127/15; C07C 157/05

[58] Field of Search ........... 260/534 M, 490, 481 R, 260/482 R, 439 R, 429.9, 448 R, 501.11, 501.12, 247.2 A, 247.1 R, 293.85, 293.86, 268 R, 326.8, 326.83, 326.85, 326.5 L, 326.5 S, 211 R; 424/311, 319

[56] References Cited  
UNITED STATES PATENTS  
3,282,987 11/1966 Ellis.............................. 260/534 M OTHER PUBLICATIONS  
Chem. Abstracts, 68:78234c.  
Chem. Abstracts, 70:37755w.  
Chem. Abstracts, 47:3873g.

Primary Examiner—Vivian Garner  
Attorney, Agent, or Firm—Thomas E. Arther; Harry E. Westlake, Jr.; Rudolph J. Anderson, Jr.

[57] ABSTRACT

This invention relates to 8,10-diaza-9-oxo(and thioxo-)-11,12-secoprostaglandins and processes for their manufacture. These compounds have prostaglandin-like biological activity and are particularly useful as renal vasodilators, and for the prevention of thrombus formation.

30 Claims, No Drawings

11,12-SECOPROSTAGLANDINS

This application is a continuation-in-part of copending U.S. Ser. No. 407,008, filed Oct. 17, 1973, now abandoned.

SUMMARY OF THE INVENTION:

This invention relates to novel 8,10-diaza-9-oxo(and thioxo)-11,12-secoprostaglandins. These compounds can be represented by the following structural formula:

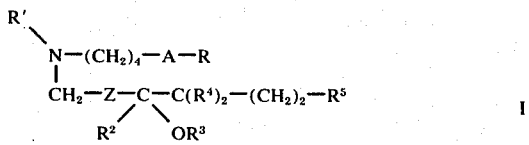

I wherein R is selected from the group consisting of carboxy and a carboxy salt being formed from a pharmaceutically acceptable cation, such as metal cations derived from alkali metals, alkaline earth metals and amines such as ammonia, primary and secondary amines and quaternary ammonium hydroxides. Especially preferred metal cations are those derived from alkali metals, e.g., sodium, potassium, lithium, and the like and alkaline earth metals, e.g., calcium, magnesium, and the like and other metals, i.e., aluminum, iron and zinc.

Pharmaceutically acceptable cations derived from primary, secondary, or tertiary amines, or quaternary ammonium hydroxides are methylamine, dimethylamine, trimethylamine, ethylamine, N-methylhexylamine, benzylamine, α-phenethylamine, ethylenediamine, piperidine, morpholine, pyrrolidine, 1,4-dimethylpiperazine, ethanolamine, diethanolamine, triethanolamine, tris(hydroxymethyl)aminomethane, N-methylglucamine, N-methylglucosamine, ephedrine, procaine, tetramethylammonium hydroxide, tetraethylammonium hydroxide, benzyltrimethylammonium and the like.

R is also selected from alkoxycarbonyl (-COOAlk) wherein Alk is alkyl having 1-10 carbon atoms, carbamoyl (—CONH$_2$), substituted carbamoyl (—CONR$^6$R$^7$) wherein R$^6$ and R$^7$ are selected from the group consisting of hydrogen, lower alkyl having 1-4 carbon atoms and diloweralkylaminoalkyl having 4-7 carbon atoms; and carbazoyl (—CONHNH$_2$).

A is selected from the group consisting of ethylene (—CH$_2$CH$_2$—), trimethylene (—CH$_2$CH$_2$CH$_2$—), α-methylethylene (—CH$_2$—CH(CH$_3$)—), β-methylethylene (—CH(CH$_3$)CH$_2$—), α,α-dimethylethylene (—CH$_2$—C(CH$_3$)$_2$—), β,β-dimethylethylene (—C(CH$_3$)$_2$CH$_2$—) and oxymethylene (—O—CH$_2$—). (Note that when A consists of a two carbon bridge, the term "α" refers to the carbon adjacent to R, while "β" refers to the other carbon atom.)

R' is selected from the group consisting of carbamoyl and thiocarbamoyl.

Z is selected from the group consisting of methylene, ethylene, trimethylene, tetramethylene, vinylene (—CH=CH—), and ethynylene (—C≡C—).

R$^2$ is independently selected from the group consisting of hydrogen and methyl.

R$^3$ is selected from the group consisting of hydrogen, and lower alkanoyl of 1–5 carbon atoms, e.g., formyl, acetyl, propionyl, butyryl, isobutyryl, valeryl, pivaloyl, and the like.

R$^4$ is selected independently from the group consisting of hydrogen and methyl.

R$^5$ is selected from the group consisting of hydrogen, lower alkyl of 1–4 carbon atoms either straight or branched (e.g., methyl, ethyl, propyl, isopropyl, butyl, tert-butyl), vinyl and 2,2,2-trifluoroethyl.

In addition, when R$^5$ is lower alkyl and R$^2$ is methyl, they can be joined together (with abstraction of hydrogen) to form a carbocyclic ring with from 6 to 9 members.

Also, when R$^5$ is lower alkyl and R$^2$ is hydrogen, R$^5$ can be joined to the carbon atom bearing R$^2$ and OR$^3$ to form a carbocyclic ring with from 5 to 8 members.

A preferred embodiment of this invention relates to the 11,12-secoprostaglandins having the following general formula:

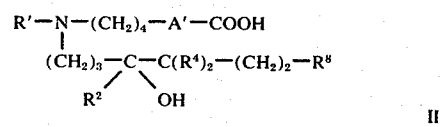

II wherein A' is ethylene or oxymethylene; R', R$^2$, and R$^4$ are as defined above; and R$^8$ is lower alkyl of 1–4 carbon atoms. In addition, when R$^2$ is methyl, R$^8$ and R$^2$ can be joined together to form a carbocyclic ring with from 6 to 9 members. Also, when R$^2$ is hydrogen, R$^8$ can be joined to the carbon bearing R$^2$ to form a carbocyclic ring with from 5 to 8 members.

It is to be noted that the carbon atom bearing the OR$^3$ group in formula I and the one bearing the hydroxyl group in formula II is asymmetric. This invention also covers stereoisomers in which the asymmetric center is exclusively in either one or the other of the two possible configurations, R and S.

BACKGROUND OF THE INVENTION

The compounds of formula I are described as 8,10-diaza-9-oxo(and thioxo)-11,12-secoprostaglandins because of their structural relationship to the naturally-occurring prostaglandins.

The prostaglandins constitute a biologically prominent class of naturally occurring, highly functionalized C$_{20}$ fatty acids which are anabolized readily in a diverse array of mammalian tissues from three essential fatty acids; namely, 8,11,14-eicosatrienoic acid, 5,8, 11,14-eicosatetraenoic acid and 5,8,11,14,17-eicosapentaenoic acid. Each known prostaglandin is a formal derivative of the parent compound, termed "prostanoic acid"; the latter is a C$_{20}$ fatty acid covalently bridged between carbons 8 and 12 such as to form a trans, vicinally-substituted cyclopentane in which the carboxy-bearing side chain is "alpha" or below the plane of the ring and the other side chain is "beta" or above the plane of the ring as depicted in formula III:

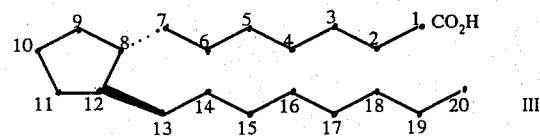

III

The six known primary prostaglandins, $PGE_1$, $PGE_2$, $PGE_3$, $PGF_{1\alpha}$, $PGF_{2\alpha}$, and $PGF_{3\alpha}$, resulting directly from anabolism of the above cited essential fatty acids via the action of prostaglandin synthetase, as well as the three prostaglandins resulting from in vivo dehydration of the PGE's, i.e., $PGA_1$, $PGA_2$, and $PGA_3$, are divided into three groups; namely, the PGE, PGF, and PGA series on the basis of three distinct cyclopentane nuclear substitution patterns as illustrated as follows:

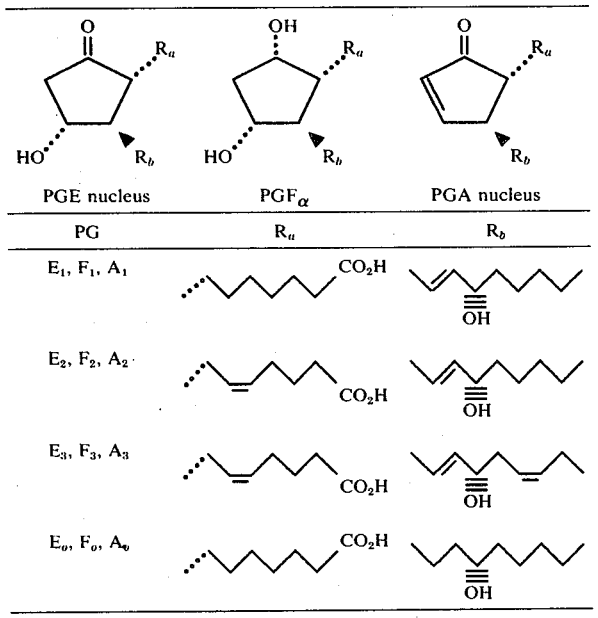

It should be noted that the Arabic subscripts designate the number of carbon-carbon double bonds in the designated compound and that the Greek subscript used in the PGF series designates the stereochemistry of the C-9 hydroxyl group.

Although the prostaglandins were discovered independently in the mid-1930's by Goldblatt [J. Chem. Soc. Chem. Ind. Lond., 52, 1056 (1933)] in England and Von Euler [Arch. Exp. Path. Pharmark., 175, 78 (1934)] in Sweden, these complex natural products received little attention from the scientific community until the early 1960's which coincides with the advent of modern instrumentation (e.g., mass spectrometry) which, in turn, was requisite for their successful isolation and structural elucidation by Bergström and colleagues [see Angew. Chem. Int. Ed., 4, 410 (1965) and references cited therein for an account of this work]. Within the last decade, a massive international scientific effort has been expended in developing both biosynthetic and chemical routes to the prostaglandins and, subsequently, in investigating of their biological activities. During this period, prostaglandins have been shown to occur extensively in low concentrations in a myriad of mammalian tissues where they are both rapidly anabolized and catabolized and to exhibit a vast spectrum of pharmacological activities including prominent roles in (a) functional hyperemia, (b) the inflammatory response, (c) the central nervous system, (d) transport of water and electrolytes, and (e) regulation of cyclic AMP. Further details concerning the prostaglandins can be found in recent reviews of their chemistry [J. E. Pike, Fortschr. Chem. Org. Naturst., 28, (1970) and G. F. Bundy, A. Rep. in Med. Chem., 7, 157 (1972)], biochemistry [J. W. Hinman, A. Rev. Biochem., 41, 161 (1972)], physiological significance [E. W. Horton, Physiol. Rev., 49, 122 (1969)] and general clinical application [J. W. Hinman, Postgrad. Med. J., 46, 562 (1970)].

The potential application of natural prostaglandins as medicinally useful therapeutic agents in various mammalian disease states is obvious but suffers from three formidable major disadvantages, namely, (a) prostaglandins are known to be rapidly metabolized in vivo in various mammalian tissues to a variety of metabolites which are devoid of the desired original biological activities, (b) the natural prostaglandins are inherently devoid of biological specificity which is requisite for a successful drug, and (c) although limited quantities of prostaglandins are presently produced by both chemical and biochemical processes, their production cost is extremely high; and, consequently, their availability is quite restricted.

Our interest has, therefore, been to synthesize novel compounds structurally related to the natural prostaglandins but with the following unique advantages: (a) simplicity of synthesis leading to low cost of production; (b) specificity of biological activity which may be either of a prostaglandin-mimicking or prostaglandin-antagonizing type; (c) enhanced metabolic stability. The combination of these advantages serves to provide effective, orally and parenterally active therapeutic agents for the treatment of a variety of human and animal diseases.

More specifically, in the clinic, prostaglandin agonists can function as agents for improving renal function (e.g., renal vasodilation), agents for the treatment and prophylaxis of certain autoimmune diseases and hypersensitivity conditions, anti-ulcer agents, agents for fertility control, antithrombotics, antiasthmatics, antilipolytics, antineoplastic agents, and agents for the treatment of certain skin diseases.

Prostaglandin antagonists can function as antiinflammatory agents, anti-diarrheal agents, antipyretics, agents for prevention of premature labor, and agents for the treatment of headache.

The compounds of the present invention are useful as pharmaceutically active compounds. Thus, these compounds are orally active in the treatment of conditions which are responsive to the actions of the natural prostaglandins. It is of course necessary to determine by routine laboratory testing which of the compounds of the present invention are most suitable for a specific end use. Some of the compounds of the invention have prostaglandinlike activity in that they mimic the effect of prostaglandin $E_1$ in stimulating the formation of cyclic AMP in the mouse ovary in vitro.

Certain of the compounds of this invention, e.g., 7-[1-(4-hydroxynonyl)ureido]heptanoic acid, mimic the effects of prostaglandin $E_1$ in producing increased renal blood flow (renal vasodilation) in laboratory animals and can be used to improve renal function in animals with poorly functioning kidneys.

Also, certain of the compounds of this invention are effective in inhibiting the aggregation of platelets in blood stimulated with collagen to cause platelet aggregation, and thus, in inhibiting platelet aggregation, are useful in preventing thrombus formation. An example of such a compound is 7-[1-(4-hydroxynonyl)-thioureido]-heptanoic acid.

Because of their biological activity and ready accessibility, the compounds of the invention are also useful in that they permit large scale animal testing useful and necessary to understanding of these various disease conditions such as kidney impairment, ulcers, dwarfism caused by poorly functioning pituitary glands, stroke (thrombus formation), and the like. It will be appreciated that not all of the compounds of this invention have these biological activities to the same degree but the choice of any particular ones for any given purpose will depend upon several factors including the disease state to be treated.

The compounds of this invention can be administered either topically or systemically, i.e., intravenously, subcutaneously, intramuscularly, orally, rectally, or by aerosolization in the form of sterile implants for long action. They can be formulated in any of a number of pharmaceutical compositions and non-toxic carriers to this end.

The pharmaceutical compositions can be sterile injectable suspensions or solutions, or solid orally administrable pharmaceutically acceptable tablets or capsules; the compositions can also be intended for sublingual administration, or for suppository use. It is especially advantageous to formulate compositions in dosage unit forms for ease and economy of administration and uniformity of dosage. "Dosage unit form" as a term used herein refers to physically discrete units suitable as unitary dosages for animal and human subjects, each unit containing a predetermined quantity of active material calculated to produce the desired biological effect in association with the required pharmaceutical means.

Illustratively, a sterile injectable composition can be in the form of aqueous or oleagenous suspensions or solutions.

The sterile injectable composition can be aqueous or oleagenous suspension or solution. Suspensions can be formulated according to the known art using suitable dispersing and wetting agents and suspending agents. Solutions are similarly prepared from the salt form of the compound. For the laboratory animals, we prefer to use incomplete Freund's adjuvant or sterile saline (9%) as carrier. For human parenteral use, such as intramuscularly, intravenously, or by regional perfusion, the diluent can be a sterile aqueous vehicle containing a preservative; for example, methylparaben, propylparaben, phenol, and chlorobutanol. The aqueous vehicle can also contain sodium chloride, preferably in an amount to be isotonic; as well as a suspending agent, for example, gum arabic, polyvinyl pyrrolidone, methyl cellulose, acetylated monoglyceride (available commercially as Myvacet from Distillation Products Industry, a division of Eastman Kodak Company), monomethyl glyceride, dimethyl glyceride or a moderately high molecular weight polysorbitan (commercially available under the tradenames Tween or Span from Atlas Powder Company, Wilmington, Delaware). Other materials employed in the preparation of chemotherapeutic compositions containing the compound may include glutathione, 1,2-propanediol, glycerol and glucose. Additionally, the pH of the composition is adjusted by use of an aqueous solution such as tris(hydroxymethyl)aminomethane (tris buffer).

Oily pharmaceutical carriers can also be used, since they dissolve the compound and permit high doses. Many oily carriers are commonly employed in pharmaceutical use, such as, for example, mineral oil, lard, cottonseed oil, peanut oil, sesame oil, or the like.

It is preferred to prepare the compositions, whether aqueous or oils, in a concentration in the range of from 2-50 mg./ml. Lower concentrations require needless quantities of liquid. Higher concentrations than 50 mg./ml. are difficult to maintain and are preferably avoided.

Oral administration forms of the drug can also be prepared for laboratory animals or human patients provided that they are encapsulated for delivery in the gut. The drug is subject to enzymatic breakdown in the acid environment of the stomach. The same dosage levels can be used as for injectable forms; however, even higher levels can be used to compensate for biodegradation in the transport. Generally, a solid unit dosage form can be prepared containing from 0.5 mg. to 25 mg. active ingredient.

Whatever the mode of administration, doses in the range of about 0.10 to 20 milligrams per kilogram of body weight administered one to four times per day are used. The exact dose depending on the age, weight, and condition of the patient, and the frequency and route of administration.

The low cost and ready accessibility of the compounds of this invention make them particularly promising for applications in veterinary medicine in which field their utilities are comparable to those in human medicine.

PROCESSES FOR THE SYNTHESIS OF COMPOUNDS OF THE INVENTION

The synthesis of compounds of the type represented by formula I wherein R is carboxy, $R^3$ is hydrogen, and R' is carbamoyl (formula IVa) is carried out by the base-catalyzed hydrolysis of a compound of formula V. The starting material is dissolved in a solvent, such as ethanol, containing a base, such as sodium ethoxide and treating with a slight excess of one molecular equivalent of hydrogen peroxide.

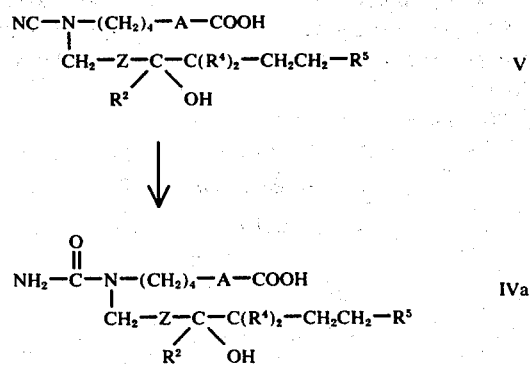

The reaction mixture is then allowed to stand at a temperature of 15° to 55° C. for a period of one to sixty hours. The product is isolated by diluting the reaction mixture with water, acidifying with a mineral acid, such as hydrochloric acid, and extracting the product with an appropriate organic solvent, such as methylene chloride. The product can be isolated by evaporation of the solvent. If purification is necessary, it can be effected by recrystallization (if the product is a solid) or by chromatography.

The synthesis of compounds of type represented by formula I wherein R is carboxy; $R^3$ is hydrogen; and R' is thiocarbamoyl (formula IV b) is carried out by treating a compound of formula V:

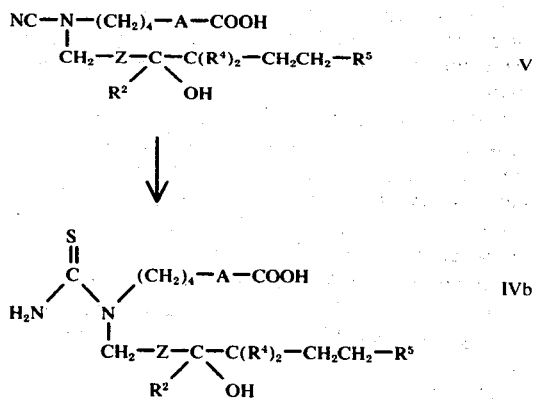

with a thiol aliphatic acid of 1–5 carbon atoms in the presence of a free radical-initiator catalyst, followed by mild basic hydrolysis.

The starting compound is first dissolved in thioacetic acid and irradiated the resulting solution using a lamp capable of generating ultraviolet light for a period of from one to twelve hours. After the solvent is removed by evaporation in vacuo, the residue is dissolved in aqueous ammonium hydroxide solution and stirred at a temperature of 15° to 35° C. for a period of 24 to 72 hours. After cooling and acidification with a mineral acid such as hydrochloric acid, the product separates which is purified by chromatography.

Compounds of the type represented by formula V are prepared by the mild hydrolysis of compounds of formula VI using a base, such as an alkali metal hydroxide, i.e., sodium hydroxide, in a solvent, such as an alcohol, i.e., methanol or ethanol, and stirring the mixture for a period of 5 to 40 hours at a temperature of 15°–35° C. The product is isolated by diluting with water, acidifying with a mineral acid, such as hydrochloric acid, and extracting the product with an appropriate organic solvent, such as ethyl acetate, and evaporating the solvent.

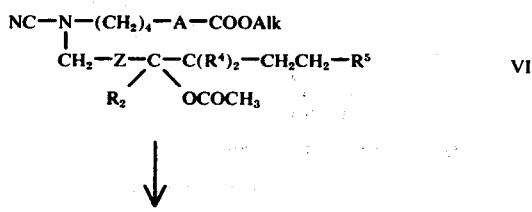

The synthesis of compounds represented by formula VI can be carried out by either of two methods. The first method involves the reaction of the alkali metal salt of formula VII with a compound of formula VIII (where X represents halogen and M represents an alkali metal ion):

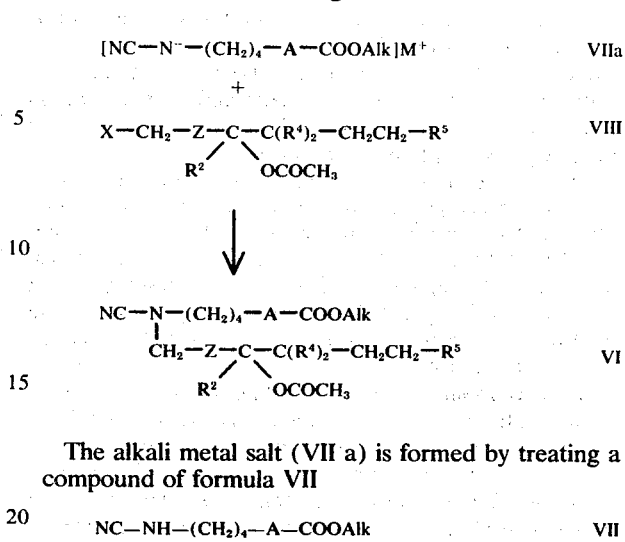

The alkali metal salt (VII a) is formed by treating a compound of formula VII $$NC-NH-(CH_2)_4-A-COOAlk \qquad VII$$

with sodium hydride in a solvent, such as a 1:1 mixture of benzene and dimethylformamide. After the salt is formed, compound VIII is added at ambient temperature and the mixture stirred and heated at 50°–100° C. for 10 to 24 hours. The product is isolated by pouring the reaction mixture into water, extracting with benzene and evaporating the solvent. Purification is effected by chromatography using silica gel.

The second method for the synthesis of compounds of formula VI involves the reaction of an alkali metal salt of formula IXa with a compound of formula X. The alkali metal salt (IX a)

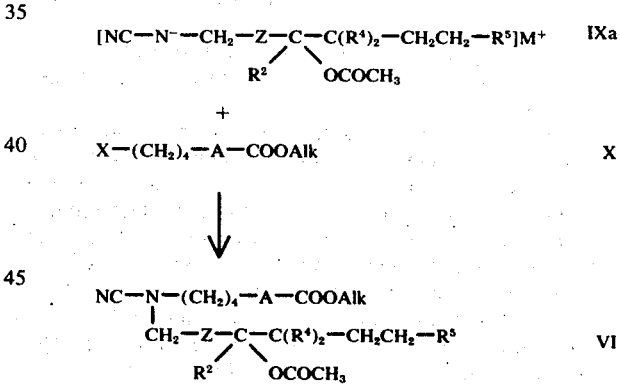

is formed by treating a compound of formula IX with sodium hydride in a solvent such as a 1:1 mixture of

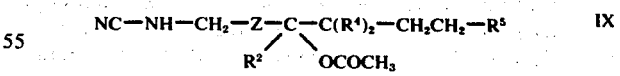

benzene and dimethylformamide. After the salt is formed, compound X is added at ambient temperature and the reaction mixture is heated at 35°–100° C. for 1 to 48 hours and the product is isolated by the procedure described for the first method.

It is frequently advantageous from a therapeutic standpoint to prepare compounds of this invention (formula I) in which the asymmetric carbon atom which bears the $OR^3$ group is exclusively in the R or S configuration. It will be recalled that the corresponding atom in the natural prostaglandins is in the S configuration. Inversion of this center may or may not produce a reduction in biological activity, although a marked increase in biological specificity is often realized.

In our series of 8,10-diaza-11,12-secoprostaglandins, compounds which are exclusively R or S at this center can be produced by employing preresolved compounds of formula VIII or IX and carrying out the steps of process described above. An example of the use of such a presolved compound IV is given under the section "Preparation of Intermediates (Example J and K)".

DERIVATIZATION OF PRODUCTS

The directly obtained products of the process described supra can be derivatized to yield the other products of formula I.

1. The fundamental processes yield compounds where R is carboxy. To obtain carboxy salts the acid products are dissolved in a solvent such as ethanol, methanol, glyme and the like and the solution treated with an appropriate alkali or alkaline earth hydroxide or alkoxide to yield the metal salt, or with an equivalent quantity or ammonia, amine or quaternary ammonium hydroxide to yield the amine salt. In each instance, the salt either separates from the solution and may be separated by filtration or, when the salt is soluble it may be recovered by evaporation of the solvent. Aqueous solutions of the carboxylic acid salts can be prepared by treating an aqueous suspension of the carboxylic acid with an equivalent amount of an alkaline earth hydroxide or oxide, alkali metal hydroxide, carbonate or bicarbonate, ammonia, an amine or a quarternary ammonium hydroxide.

To obtain carboxy esters (i.e., compounds where R is alkoxycarbonyl) the acid products are treated in ether with an ethereal solution of the appropriate diazoalkane. For example, methyl esters are produced by reaction of the acid products with diazomethane. To obtain products where R is carbamoyl or substituted carbamoyl, the acid product is first converted to an active Woodward ester. For example, the acid product can be made to react with N-tert-butyl-5-methylisoxazolium perchlorate in acetonitrile in the presence of a base such as triethylamine to yield an active ester in which R is

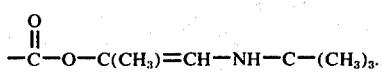

Active esters of this type can be reacted with ammonia to yield products of formula I where R is carbamoyl, with primary or secondary amines or di-loweralkylaminoalkylamines to yield products where R is substituted carbamoyl, i.e., —CONR$^6$R$^7$.

2. The fundamental process yields products where R$^3$ is hydrogen. In compounds of formulas IVa and IVb reaction with formic acid, acetic anhydride, propionic anhydride, butyric anhydride, isobutyric anhydride, valeric anhydride, pivalic anhydride and the like, without solvent and at temperatures from 25° to 60° C., gives compounds wherein R$^3$ is formyl, acetyl, propionyl, butyryl, isobutyryl, valeryl, and pivaloyl, respectively.

PREPARATION OF STARTING MATERIALS

1. Reagents of formula VII are prepared by a three-step process from compounds of formula XII. Treatment of compounds of formula XII with potassium cyanate in water, followed by heating the solution at 50° C. to 100° C. for one to 5 hours, cooling and adjusting the pH to about 5 with mineral acid gives the ureido compound (formula XIII). Esterification of

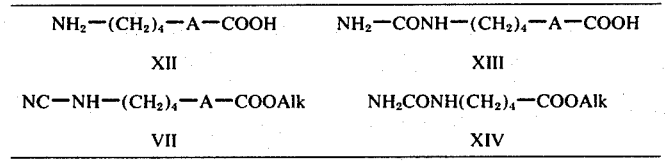

compound XIII with a loweralkanol and an acid under conventional esterification conditions provides the corresponding ester (formula XIV) which is dehydrated using p-toluene-sulfonyl chloride in pyridine. In instances where the amino acids of formula XII are not known, they may be prepared from the known halo acids X by the classic phthalimide synthesis (where X is halogen)

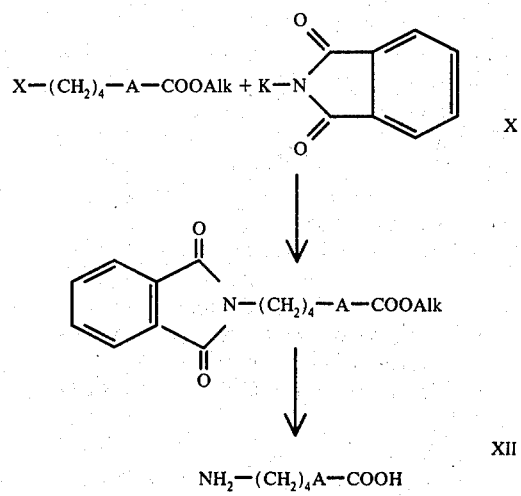

2. The reagent VIII a which has the following general formula wherein X is halogen and R$^4$ and R$^5$ are as

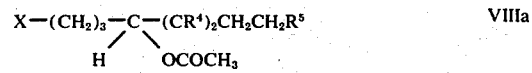

previously defined is prepared in the following manner. A Grignard reagent R$^5$CH$_2$CH$_2$(R$^4$)$_2$C—MgI or R$^5$CH$_2$CH$_2$(R$^4$)$_2$—MgBr is allowed to react, in ether, with a nitrile X(CH$_2$)$_3$CN. The resulting imine is hydrolyzed in aqueous acidic solution to give ketones of the formula XI:

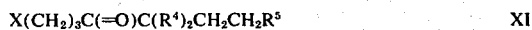

The ketones (XI) are reduced to the corresponding alcohols X(CH$_2$)$_3$CH(OH)—C(R$^4$)$_2$CH$_2$CH$_2$R$^5$ with sodium or potassium borohydride in a suitable solvent such as methanol, ethanol, or diglyme. Acetylation of these alcohols, preferably with acetic anhydride, yields the reagents VIII A.

By treatment of ketone XI with methylmagnesium iodide ($CH_3MgI$) in ether, compounds of formula $X(CH_2)_3C(CH_3)(OH)C(R^4)_2CH_2CH_2R^5$ are obtained which upon acylation with acetic anhydride in pyridine gives compounds of formula VIII b:

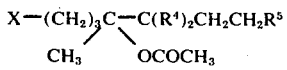  VIIIb

The reagents VIII c which have the following general formula:

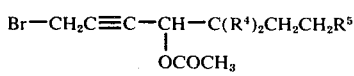  VIIIc wherein X and $R^4$ and $R^5$ are defined previously are prepared in the following manner. Acetylenic alcohols $HC \equiv C-CH(OH)C(R^4)_2CH_2CH_2R^5$ are treated with acetic anhydride to give the acetylated alcohols

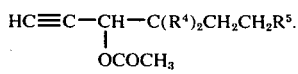

These compounds are treated with paraformaldehyde and diethylamine to afford the tertiary amines

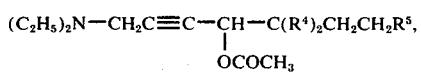

which when treated with cyanogen bromide yield the reagents VIII c. The acetylenic alcohols $HC \equiv C-CH(OH)-C(R^4)_2CH_2CH_2R^5$ intermediates for compounds of formula VIII c are prepared by reaction of ethynylmagnesium bromide or lithium acetylide with aldehydes of the formula $R^5CH_2CH_2C(R^4)_2CHO$.

By using the resolved R and S forms of the alcohols $HC \equiv C-CH(OH)C(R^4)_2CH_2CH_2R^5$ in the above scheme, the corresponding R and S forms of the reagent VIII c can be obtained.

It should be noted here that the use of the R or S enantiomers of reagent VIII c produce the R and S enantiomers, respectively, of compounds of formula V wherein $R^4$, and $R^5$ are as defined previously and $R^2$ is H and $Z^1$ is $-C \equiv C-$ (formula Va).

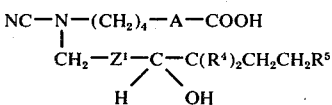  Va

These optically active products Va can be hydrogenated over a platinum catalyst to give the R and S enantiomers of compounds of formula Va where Z is ethylene $-CH_2-CH_2-$.

The reagent VIII d which has the following general formula:

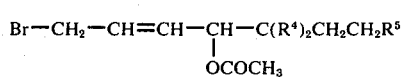  VIIId wherein X, $R^4$ and $R^5$ are as defined above, are prepared in the following manner. A Grignard reagent $R^5CH_2CH_2C(R^4)_2MgBr$ or $R^5CH_2CH_2C(R^4)_2MgI$ is allowed to react with crotonaldehyde to give, after hydrolysis, the alcohol $CH_3CH=CH-CH(OH)-C(R^4)_2CH_2CH_2R^5$. This alcohol is acetylated, preferably with acetic anhydride without solvent at 30°–100° C. for 2–12 hours, to give the intermediate $CH_3CH=CH-CH(OCOCH_3)C(R^4)_2CH_2CH_2R^5$. This intermediate is allowed to react with N-bromosuccinimide in chloroform at 50°–70° C. for 2.5 to 5 hours to effect allylic bromination and give the reagent of formula VIII d.

3. The reagent IX in which $R^2$ is H (IX b) is prepared by the following reactions. The alcohol prepared

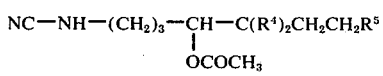  IXb in Section 2 above with the formula

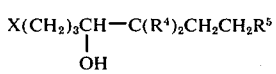

is treated with dihydropyran and a catalytic amount of acid to give

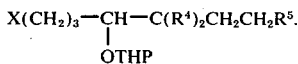

Treatment of this halo compound with the sodium salt of phthalimide in dimethylformamide affords the corresponding phthalimido compound. Cleavage of this compound with hydrazine in ethanol followed by acid hydrolysis yields the amine

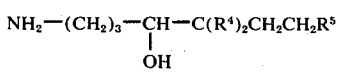

which upon treatment with potassium cyanate in water yields the corresponding hydroxy urea which is acetylated and then dehydrated with p-toluenesulfonyl chloride in pyridine to give the reagent IX.

4. The preparation of reagents of formula X has been described in the scientific and patent literature in instances

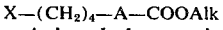  X where A is ethylene, trimethylene, α-methylethylene, β-methylethylene, α,α-dimethylethylene, β,β-dimethylethylene. To prepare reagents where A is oxymethylene, an ester of glycolic acid, $HOCH_2COOAlk$ is treated with a strong base, preferably sodium hydride, in a non-protic solvent (dimethylformamide, glyme, and the like) and the resulting anion caused to react with a 1,4-dihalobutane, preferably 1,4-dibromobutane. The glycolic ester and base are employed in approximately equimolar quantities; a 1.5 to 2 molar excess of the dihalobutane is advantageously used.

5. Methods for obtaining optical antipodes of some compounds of this invention have been described supra whereby one of the components of the molecule is preresolved prior to its assembly into the whole molecule. Other methods also can be employed; for example, mixtures of racemates may be separated by taking advantage of the physiochemical differences between the components using chromatography and/or fractional crystallization. The racemic products and intermediates of this invention can be resolved into their optically active components by any one of a number of methods of resolution which are well described in the chemical literature.

Those compounds which are carboxylic acids can be converted to the diastereoisomeric salts by treatment with an optically active base such as + or − α-methylbenzylamine, + or − α-(1-naphthyl)-ethylamine, brucine, cinchonine, cinchonidine, or quinine. These diastereoisomeric salts can be separated by fractional crystallization.

The carboxylic acids of this invention also can be converted to esters using an optically active alcohol, such as, estradiol-3-acetate, or d- or l-menthol and the diastereoisomeric esters resolved by crystallization or by chromatographic separation.

Racemic carboxylic acids also may be resolved by reverse phase and absorption chromatography using an optically active support and absorbent.

Compounds of this invention which contain free hydroxyl groups can be esterified with acid chlorides or anhydrides derived from optically active acids, such as, (+)-10-camphorsulfonic acid, (+)-α-bromocamphor-λ-sulfonic acid, or d- or 1-6,6'-dinitrodiphenic acid to form esters which can be resolved by crystallization.

Another method of obtaining pure optical isomers involves incubation of the racemic mixture with certain microorganisms such as fungi, by processes well established in the art, and recovering the product formed by the enzymatic transformation.

The methods described supra are especially effective if one applies the process to a compound where one asymmetric center has been preresolved by the techniques already described.

This invention is further described in the following examples.

PREPARATION OF INTERMEDIATES

A. Preparation of 1-Chloro-4-acetoxynonane

Step 1. Preparation of 1-Chloro-4-nonanone

To the Grignard reagent prepared from a mixture of amyl bromide (226.59 g.; 1.5 moles) and magnesium (36.48 g.; 1.5 moles) in ether (1000 ml.) is added, dropwise, during 1 hour, 4-chlorobutyronitrile (155.34 g.; 1.5 moles). Stirring is continued for an additional one hour. The reaction mixture is poured into a mixture of finely crushed ice (1000 g.) and concentrated hydrochloric acid (750 ml.). The ether layer is separated quickly and discarded. The aqueous layer is heated on a steam bath for 1 hour to hydrolyze the intermediate imine and cause the separation of the ketone as an oil. After cooling, the oil is extracted with ether and the combined extracts are washed with saturated sodium chloride solution and dried over anhydrous sodium sulfate. The solvent is removed under vacuum and the residual oil is distilled to give 69.0 g. (26%) of colorless oil, b.p. 115°–117°/14 mm.; pmr (CDCl$_3$)δ 0.90 (3H,t), 3.56 (2H,t, CH$_2$Cl).

Step 2. Preparation of 1-Chloro-4-nonanol

A suspension of sodium borohydride (6.62 g.; 0.175 mole) and sodium hydroxide (1.3 g.) in ethanol (310 ml.) is treated, dropwise, over 1 hour with 1-chloro-4-nonanone (61.40 g.; 0.349 mole) while the temperature is maintained at 45°–50° C. Stirring is continued for one hour, longer without external cooling.

The reaction mixture is acidified with concentrated hydrochloric acid to the Congo red endpoint and then the ethanol is removed under reduced pressure. The residue is treated with water (200 ml.) and the resulting oil is extracted with ether. The combined extracts are washed with saturated sodium chloride solution and dried over anhydrous sodium sulfate. The solvent is removed under vacuum to give the title compound as a light yellow residual oil, yield 58.85 g.; ir (neat) 3400 cm$^{-1}$.

Step 3. Preparation of 1-Chloro-4acetoxynonane

A mixture of 1-chloro-4-nonanol (111.99 g.; 0.627 mole) and acetic anhydride (128.0 g.; 1.254 moles) is heated on a steam bath for 1½ hours.

The volatile materials are removed under reduced pressure and the residual oil is distilled to give 88.6 g. (64%) of colorless oil, b.p. 130°–133°/14 mm.; pmr (CDCl$_3$) δ 0.89 (3H,t), 2.02 (3H,s CH$_3$COO), 3.53 (2H,t CH$_2$Cl), 4.89 (1H,m).

Anal. Calcd. for C$_{11}$H$_{21}$ClO$_2$: C, 59.85; H, 9.59. Found: C, 59.87; H, 9.67.

B. Preparation of 1-Chloro-4-acetoxy-8-methylnonane

Step 1. Preparation of 1-Chloro-8-methyl-4-nonanone

To the Grignard reagent prepared from a mixture of 1-bromo-4-methylpentane (200.00 g.; 1.21 mole) and magnesium (29.43 g.; 1.21 mole) in ether (800 ml.) is added, dropwise during one hour, 4-chlorobutyronitrile (125.30 g.; 1.21 mole). Stirring is continued for an additional one hour.

The reaction mixture is poured into a mixture of finely crushed ice (800 g.) and concentrated hydrochloric acid (600 ml.). The ether layer is separated quickly and discarded. The aqueous layer is heated on a steam bath for one hour to hydrolyze the intermediate imine and cause the separation of the ketone as an oil. After cooling, the oil is extracted with ether and the combined extracts are washed with saturated sodium chloride solution and dried over anhydrous sodium sulfate. The solvent is removed under vacuum and the residual oil is distilled to give 23.3 g. (10%) of colorless oil, b.p. 121°–122°/15 mm.; pmr (CDCl$_3$) δ 0.89 (6H,d), 3.57 (2H,t CH$_2$Cl).

Anal. Calcd. for C$_{10}$H$_{19}$ClO: C, 62.98; H, 10.04. Found: C, 62.86; H, 10.20.

Step 2. Preparation of 1-Chloro-8-methyl-4-nonanol

A suspension of sodium borohydride (2.3 g., 0.061 mole) and sodium hydroxide (0.5 g.) in ethanol (110 ml.) is treated dropwise during one hour with 1-chloro-8-methyl-4-nonanone (23.0 g., 0.121 mole) while the temperature is maintained at 45°–50° C. Stirring is continued for one hour longer without external cooling.

The reaction mixture is acidified with concentrated hydrochloric acid to the Congo red endpoint and then the ethanol is removed under reduced pressure. The residue is treated with water (70 ml.) resulting oil is extracted with ether. The combined extracts are washed with saturated sodium chloride solution and dried over anhydrous sodium sulfate. The solvent is removed under vacuum to give the title compound as a light yellow residual oil, yield 22.73 g.; ir (neat) 3400 cm$^{-1}$.

Step 3. Preparation of 1-Chloro-4-acetoxy-8-methylnonane

A mixture of 1-chloro-8-methyl-4-nonanol (22.73 g.; 0.118 mole) and acetic anhydride (24.07 g.; 0.236 mole) is heated on a steam bath for 1½ hours.

The volatile materials are removed under reduced pressure and the residual oil is distilled to give 14.58 g. (58%) of colorless oil, b.p. 138°–139°/15 mm.; pmr (CDCl$_3$) δ 0.85 (6H,d), 2.02 (3H,s CH$_3$COO), 3.53 (2H,t CH$_2$Cl), 4.92 (1H,m).

C. Preparation of 1-Chloro-4-acetoxyundecane

Step 1. Preparation of 1-Chloro-4-undecanone

This compound is prepared essentially by the same procedure as described for 1-chloro-4-nonanone (Example A, Step 1) using the following reagents:

| | |
|---|---|
| 1-Bromoheptane | 214.94 g. (1.2 mole) |
| Magnesium | 29.18 g. (1.2 mole) |
| Ether | 800 ml. |
| 4-Chlorobutyronitrile | 124.27 g. (1.2 mole) |

The title compound is obtained as a colorless oil, yield 60.4 g. (15%), b.p. 135°–140°/15 mm.; pmr (CDCl$_3$) δ 0.93, (3H,t), 3.57 (2H,t CH$_2$Cl).

Step 2. Preparation of 1-Chloro-4-undecanol

This compound is prepared essentially by the same procedure as described for 1-chloro-4-nonanol (Example A, Step 2) using the following reagents:

| | |
|---|---|
| Sodium borohydride | 5.56 g. (0.147 mole) |
| Sodium hydroxide | 1.12 g. |
| Ethanol | 265 ml. |
| 1-Chloro-4-undecanone | 60.00 g. (0.294 mole) |

The title compound is obtained as a yellow residual oil, yield 60.02 g.

Step 3. Preparation of 1-Chloro-4-acetoxyundecane

This compound is prepared essentially by the same procedure as described for 1-chloro-4-acetoxy-nonane (Example A, Step 3), using the following reagents:

| | |
|---|---|
| 1-Chloro-4-undecanol | 60.02 g. (0.29 mole) |
| Acetic anhydride | 59.16 g. (0.58 mole) |

The title compound is obtained as a colorless oil, yield 44.6 g. (62%), b.p. 155°–158°/15 mm.; pmr (CDCl$_3$) δ 0.88 (3H,t), 2.02 (3H,s CH$_3$COO), 3.53 (2H,t CH$_2$Cl), 4.92 (1H,m).

Anal. Calcd. for C$_{13}$H$_{25}$ClO$_2$: C, 62.76; H, 10.13. Found: C, 63.03; H, 10.40.

D. Preparation of 1-Chloro-4-acetoxy-8,8-dimethyl-nonane

By following the procedure described for 1-chloro-4-acetoxynonane (Example A) but substituting 1-bromo-4,4-dimethylpentane for amyl bromide, there is obtained in succession: 1-chloro-8,8-dimethyl-4-nonanone, 1-chloro-8,8-dimethyl-4-nonanol, and 1-chloro-4-acetoxy-8,8-dimethylnonane.

E. Preparation of 1-Chloro-4-acetoxy-9,9,9-trifluorononane

By following the procedure described for 1-chloro-4-acetoxynonane (Example A) but substituting 1-bromo-5,5,5-trifluoropentane for amyl bromide, there is obtained in succession: 1-chloro-9,9,9-trifluoro-4-nonanone, 1-chloro-9,9,9-trifluoro-4-nonanol, and 1-chloro-4-acetoxy-9,9,9-trifluorononane.

F. Preparation of 1-Chloro-4-acetoxy-8-nonene

By following the procedure described for 1-chloro-4-acetoxynonane (Example A) but substituting 1-bromo-4-pentene for amyl bromide, there is obtained in succession: 1-chloro-8-nonen-4-one, 1-chloro-8-nonen-4-ol, and 1-chloro-4-acetoxy-8-nonene.

G. Preparation of 1-Chloro-4-acetoxy-5,5-dimethylnonane

Step 1. Preparation of 1-Chloro-5,5-dimethyl-4-nonanone

Four hundred ml. of a solution in ether of 1,1-dimethylpentylmagnesium chloride prepared from magnesium (24.3 g., 1.0 mole) and 1-chloro-1,1-dimethylpentane (134.5 g., 1.0 mole) according to the procedure of Whitmore and Badertscher [J. Am. Chem Soc., 55, 1559 (1933)] is added dropwise with stirring to 4-chlorobutyryl chloride (197 g., 1.4 moles) in ether (400 ml) during 6 hours. The reaction mixture is stirred for an additional 12 hours. It is then poured into a mixture of ice and dilute hydrochloric acid. The ether layer is separated, washed with water and brine and dried over sodium sulfate. The ether is evaporated and the residue distilled at aspirator vacuum through a Vigreaux column to yield the product as a colorless oil.

Step 2. Preparation of 1-Chloro-5,5-dimethyl-4-nonanol

By following the procedure described for 1-chloro-4-nonanol (Example A, Step B) but substituting 1-chloro-5,5-dimethyl-4-nonanone for 1-chloro-4-nonanone and continuing stirring and heating at 50° C. for 6 hours, there is obtained 1-chloro-5,5-dimethyl-4-nonanol.

Step 3. Preparation of 1-Chloro-4-acetoxy-5,5-dimethylnonane

By following the procedure described for 1-chloro-4-acetoxynonane (Example A, Step 3) but substituting 1-chloro-5,5-dimethyl-4-nonanol for 1-chloro-4-nonanol and continuing the steam bath heating for 4 hours, there is obtained 1-chloro-4-acetoxy-5,5-dimethylnonane.

H. Preparation of 1-Bromo-4-acetoxy-2-nonene

A mixture of 4-acetoxy-2-nonene (73.5 g., 0.4 mole), N-bromosuccinimide (80.0 g., 0.45 mole), and carbon tetrachloride (500 ml.) is boiled under reflux for 3 hours. The mixture is then cooled and the suspended succinimide, removed by filtration. The carbon tetrachloride solution is washed with dilute sodium bicarbonate solution and water, and is dried over sodium sulfate. The carbon tetrachloride is evaporated in vacuo and the residual oil is distilled to yield 62 g. (59%) of 1-bromo-4-acetoxy-2-nonene as a light yellow oil, b.p. 110°–112°/0.1 mm.

I. Preparation of 1-Bromo-4-acetoxy-2-nonyne

Step 1. Preparation of 3-Acetoxy-1-octyne

1-Octyn-3-ol (100 g., 0.794 mole) is dissolved in pyridine (79 g., 1.0 mole) and acetic anhydride (81.6 g., 0.80 mole) is added dropwise with stirring during one hour. The temperature rises to 45° C. The solution is heated at 55° C. for one hour and is then cooled and poured into 200 ml., ice-cold 5% hydrochloric acid. The oily product is taken up in ether, washed with water and brine and dried over sodium sulfate. The ether is evaporated and the residual oil distilled to yield 106.4 g. (80%) of 3-acetoxy-1-octyne, b.p. 91°–92°/15 mm.

Step 2. Preparation of 1-Diethylamino-4-acetoxy-2-nonyne

A mixture of 3-acetoxy-1-octyne (58.8 g., 0.35 mole), diethylamine (28.5 g., 0.39 mole), paraformaldehyde (13.8 g., 0.46 mole) and p-dioxane (60 ml.) is heated on the steam bath under a reflux condenser for 17 hours. The resulting solution is cooled and diluted with 250 ml. of ether. The solution is extracted with 300 ml. of 5% hydrochloric acid. The acidic aqueous extract is made basic with 10% sodium hydroxide solution. The liberated amine is taken up in ether, washed with water and brine and dried over sodium sulfate. The ether is evaporated and the residual oil distilled to yield 73.1 g. (89%) of 1-diethylamino-4-acetoxy-2-nonyne, b.p. 103°–109°/0.3 mm.

Anal. calcd. for $C_{15}H_{27}NO_2$: C, 71.10; H, 10.74; N, 5.33. Found: C, 70.73; H, 11.03; N, 5.55.

Step 3. Preparation of 1-Bromo-4-acetoxy-2-nonyne

A solution of 1-diethylamino-4-acetoxy-2-nonyne (50.6 g., 0.20 mole) and cyanogen bromide (21.2 g., 0.20 mole) in ether (250 ml.) is allowed to stand at 25°–27° C. for 18 hours. The ether solution is washed with 5% hydrochloric acid solution, water and brine and dried over sodium sulfate. The ether is evaporated and the residual oil distilled. After a forerun of diethylcyanamide, there is collected 34.1 g. (65%) of 1-bromo-4-acetoxy-2-nonyne, b.p. 97°–105°10.2mm.

Anal. calcd. for $C_{11}H_{17}BrO_2$: C, 50.59; H, 6,56. Found: C, 50.54; H, 6.49.

J. Preparation of 1-Bromo-4(R)-acetoxy-2-nonyne

By following the procedure described in Example I but substituting (R)-1-octyn-3-ol $[\alpha]_D^{26} + 6.1°$ [C 3.1, CHCl$_3$] for the racemic 1-octyn-3-ol, there is obtained successively: 3(R)-acetoxy-1-octyne, $[\alpha]_D^{26} + 70°$ [C 3.1, CHCl$_3$], 1-diethylamino-4(R)-acetoxy-2-nonyne, $[\alpha]_D^{26} + 74°$ [C 3.2, CHCl$_3$], and 1-bromo-4(R)-acetoxy-2-nonyne, $[\alpha]_D^{26} + 75°$ [C 3.2, CHCl$_3$].

K. Preparation of 1-Bromo-4(S)-acetoxy-2-nonyne

By following the procedure described in Example I but substituting (S)-1-octyn-3-ol, $[\alpha]_D^{26} - 6.4°$ [C 3.3, CHCl$_3$], for the racemic 1-octyn-3-ol, there are obtained successively: 3(S)-acetoxy-1-octyne, $[\alpha]_D^{26} - 79°$ [C 3.0, CHCl$_3$], 1-diethylamino-4(S)-acetoxy-2-nonyne, $[\alpha]_D^{26} - 80°$ [C 3.3, CHCl$_3$], and 1-bromo-4(S)-acetoxy-2-nonyne, $[\alpha]_D^{26} - 83°$ [3.7, CHCl$_3$].

L. Preparation of Methyl 7-bromo-2-methylheptanoate

Step 1. Preparation of 5-Acetoxypentyl chloride

Acetic anhydride (102 g., 1 mole) is added dropwise with stirring to pentamethylene chlorohydrin (90 g., 0.74 mole). The resulting solution is heated on the steam bath for one hour and allowed to stand overnight at room temperature. The reaction mixture is distilled to yield 83.6 g. (69%) of 5-acetoxypentyl chloride, b.p. 101°–104°/20 mm.

Step 2. Preparation of Diethyl (5-Acetoxypentyl) methylmalonate

Sodium hydride (4.8 g., 0.2 mole) as a 50% suspension in mineral oil is washed with petroleum ether under nitrogen to remove the mineral oil, suspended in dry benzene (150 ml.), and the suspension cooled in an ice bath. Diethyl methylmalonate (34.8 g., 0.2 mole) dissolved in sieve dried DMF (150 ml.) is added to the suspension of sodium hydride dropwise. The mixture is allowed to stand overnight at room temperature. Potassium iodide (0.4 g.) and 5-acetoxyphenyl chloride (32.9., 0.2 mole) are then added, and the mixture is heated for 24 hours at 125° C. in an oil bath. The reaction mixture is concentrated in vacuo, diluted with ether (200 ml.), and filtered to remove sodium chloride. The filtrate is washed with brine, dried over anhydrous magnesium sulfate and concentrated to yield 39.6 g. (66%) of oily product.

Step 3. Preparation of 7-Bromo-2-methylheptanoic acid

A mixture of the crude diethyl (5-acetoxypentyl) methylmalonate (68 g., 0.23 mole) and 48% aqueous hydrobromic acid (100 ml.) is refluxed for 20 hours. The mixture is then concentrated by distillation until the internal temperature rises to 120° C.; 96 ml. of distillate (2 layers) is collected. The residual liquid is cooled, dissolved in ether, washed with brine, dried over magnesium sulfate, and the solution concentrated in vacuo to yield 54 g. of crude 7-bromo-2-methyl-heptanoic acid as a dark viscous liquid.

Step 4. Preparation of Methyl 7-Bromo-2-methylheptanoate

A solution of crude 7-bromo-2-methylheptanoic acid (54 g., 0.24 mole) and concentrated sulfuric acid (2 drops) in absolute methanol (300 ml.) is refluxed for 5 hours. After standing overnight at room temperature, the solution is concentrated in vacuo and diluted with water. The mixture is made basic by the addition of saturated sodium carbonate solution and the product taken up in ether. The ether extract is washed with water, dried over anhydrous magnesium sulfate and distilled to yield 11.8 g. (16%) of methyl 7-bromo-2-methylheptanoate, b.p. 67°–70°/0.5 mm.; pmr CDCl$_3$) δ 1.13 (3H,d 2-CH$_3$), 2.42 (1H,m CHCOOCH$_3$), 3.38 (2H,t CH$_2$Br), 3.65 (3H,s CH$_3$O).

M. Preparation of Ethyl 4-Bromobutoxyacetate

Sodium hydride (9.0 g., 0.375 mole) is suspended in 1,2-dimethoxyethane. The mixture is stirred and cooled in an ice bath while ethyl glycollate (39.0 g., 0.375 mole) is added dropwise during one hour. 1,4-Dibromobutane (108 g., 0.5 mole) is added all at once to the resulting thick suspension. The mixture is warmed gently to initiate a strongly exothermic reaction; then the mixture is heated 3 hours on the steam bath. The mixture is poured into cold water. The heavy oil layer is taken up in ether, washed with three portions of water, and dried over sodium sulfate.

Evaporation of the ether and distillation of the residual oil yields 21.3 g. (24%) of ethyl 4-bromobutoxyacetate, a colorless oil, b.p. 99°–103°/0.2 mm.

N. Preparation of Ethyl 7-cyanamidoheptanoate

Step 1. Preparation of Ethyl 7-ureidoheptanoate

To a solution of 7-aminoheptanoic acid (2.9 g., 0.02 mole) in water (20 ml.) is added a solution of potassium cyanate (1.62 g., 0.02 mole) in water (10 ml.) and this solution is made slightly acidic by the addition of 6 N-hydrochloric acid. The reaction is heated on the steam bath for one hour during which time a solid separates. The reaction is cooled and the solid collected and dried, yield is 3.1 g. and the melting point is 166° C. The solid is not purified further. The solid is dissolved in ethanol (25 ml.), benzene (100 ml.), sulfuric acid (0.2 ml.) and heated at reflux for twenty hours. The water formed is collected in a Dean-Stark trap. The reaction is cooled, poured into water (150 ml.) and then extracted with chloroform (2 × 100 ml.). The organic layer is washed with brine, dried over sodium sulfate, and the solvent removed in vacuo. The resulting solid is crystallized from butyl chloride yielding 2.4 g. (56%) melting 90°–92° C.

Anal. calcd. for $C_{10}H_{20}N_2O_3$: C, 55.53; H, 9.32; N, 12.95. Found: C, 55.82; H, 9.45; N, 12.80.

Step 2. Preparation of Ethyl 7-cyanamidoheptanoate

To a solution of ethyl 7-ureidoheptanoate (2.1 g., 0.01 mole) in pyridine (10 ml.) is added p-toluenesulfonylchloride (2.0 g., excess). The reaction is stirred at room temperature for two hours, poured into water (100 ml.), then extracted with ether (2 × 100 ml.). The ether is washed with 5% hydrochloric acid (2 × 25 ml.), brine, then dried over sodium sulfate. The solvent is removed in vacuo to give ethyl 7-cyanamidoheptanoate as a light yellow oil, yield 1.7 g. (86%).

Anal. calcd. for $C_{10}H_{18}N_2O_2$: C, 60.58; H, 9.15; N, 14.13. Found: C, 60.52; H, 9.18; N, 13.82.

O. Preparation of 4-Acetoxynonylcyanamide

Step 1. Preparation of 1-Chloro-4-(2-tetrahydropyranyloxy) nonane

To a stirred solution of 1-chloro-4-hydroxynonane (Example A, Step 2) (11.0 g., 0.062 mole) and dihydropyran (5.2 g., 0.062 mole) cooled in an ice bath is added 5 drops of hydrochloric acid (conc.). A slight exothermic reaction is noted and when this is complete the reaction is allowed to come to room temperature, then to stand for 2 hours. At the end of this period several pellets of sodium hydroxide are added and the reaction is distilled in vacuo. The yield of 1-chloro-4-(2-tetrahydropyranyloxy) nonane is 12.5 g. (77%), boiling 96°–102°/0.1 mm. Upon redistillation a boiling point of 90°–92°/0.1 mm. is obtained.

Step 2. Preparation of N-[4-(2-Tetrahydropyranyloxy)nonyl]phthalimide

Sodium hydride (53%) (1.5 g. excess) is washed with benzene three times by decantation, then dimethyl formamide (100 ml.) is added. To this stirred suspension is added a solution of phthalimide (4.3 g., 0.03 mole) in dimethyl formamide (50 ml.) at such a rate as to keep the temperature below 35° C. A clear solution is obtained and to it is added 1-chloro-4-(2-tetrahydropyranyloxy) nonane (7.8 g., 0.03 mole) and the resulting solution is stirred and heated at 95° C. for 20 hours. The reaction is then concentrated to one-half its volume in vacuo, poured into ice water (200 ml.) and extracted with ether (2 × 150 ml.). The ether is washed with 5% sodium hydroxide (2 × 50 ml.), saturated sodium chloride solution (2 × 50 ml.), then dried over sodium sulfate. Evaporation of the ether affords 4.5 g. (45%) yield of N-[4-(2-tetrahydropyranyloxy) nonyl]phthalimide melting 59°–61° C. After crystallization from cyclohexane the product melts at 62°–63° C.

Anal. calcd. for $C_{22}H_{31}NO_4$: C, 70.75; H, 8.36; N, 3.75 Found: C, 71.03; H, 8.28; N, 3.81

Step 3. Preparation of 4-(2-tetrahydropyranyloxy) nonylamine

To a solution of N-[4-(2-tetrahydropyranyloxy) nonyl]-phthalimide (33.0 g., 0.88 mole) in absolute ethanol (300 ml.), is added hydrazine (64% aqueous) (10 ml. excess) and the reaction is heated at reflux for 1.5 hours. An additional 5 ml. of hydrazine (64%) is added and reflux continued for 1.5 hours. The reaction is cooled to room temperature and the white solid that is present is removed by filtration. The filtrate is concentrated in vacuo to 75 ml., then poured into water (200 ml.). The solution is made basic with 5% sodium hydroxide and then extracted with ether (3 × 100 ml.). The ether layer is washed with saturated sodium chloride solution, then dried over sodium sulfate. The ether is Removed in vacuo and the resulting oil is distilled. The yield of 4-(2-tetrahydropyranyloxy) nonylamine is 16.0 g. (75%), boiling 100°–102°/0.1 mm.

Anal. calcd. for $C_{14}H_{29}NO_2$: C, 69.08; H, 12.01; N, 5.75. Found: C, 68.58; H, 12.42; N, 5.66.

Step 4. Preparation of 4-Acetoxynonylurea

To a stirred suspension of 4-(2-tetrahydropyranyloxy)-nonylamine (4.8 g., 0.02 mole) in water (75 ml.) is added just enough 10% hydrochloric acid to effect solution. Then potassium cyanate (1.62 g., 0.02 mole) is added and the reaction is heated gently on the steam bath for one hour, during which time an oil separates. The reaction mixture is cooled and extracted with ether (2 × 75 ml.). The ether is dried over sodium sulfate then concentrated in vacuo to give 4-hydroxynonylurea as a residual oil. The 4-hydroxynonylurea is taken up in pyridine (20 ml.) and acetic anhydride (2.0 g., 0.02 mole) is added. The reaction is stirred eight hours at room temperature then poured into water (100 ml.), and extracted with ether (2 × 100 ml.). The ether is washed with 5% hydrochloric acid, brine, and dried over sodium sulfate. Removal of the solvent in vacuo affords the subject compound as a residual oil.

Step 5. Preparation of 4-Acetoxynonylcyanamide

To a stirred solution of 4-acetoxynonylurea (2.4 g., 0.01 mole) in pyridine (10 ml.) is added p-toluene-sulfonyl chloride (2.0 g., excess) in one portion. The reaction is stirred at room temperature for six hours then poured into water (150 ml.). The aqueous mixture is extracted with ether (3 × 75 ml.), the ether is washed with 5% hydrochloric acid, brine, and dried over sodium sulfate. The solvent is removed in vacuo to give 4-acetoxynonylcyanamide as a residual oil.

P. Preparation of 1-Acetoxy-1-(3-bromo-1-propynyl)-cyclohexane

Step 1. Preparation of 1-Acetoxy-1-ethynylcyclohexane

1-Ethynylcyclohexan-1-ol (100 g., 0.8 mole) is added dropwise with stirring to a mixture of acetic anhydride (86.7 g., 0.85 mole) and sulfuric acid (0.25 ml.). The temperature of the reaction mixture is kept at 10°–12° C. during the addition by means of an ice bath. The mixture is then stirred without cooling for 1.5 hr. It is then poured into 300 ml. of ice water. The oily product is taken up in ether, washed with water, dilute sodium bicarbonate solution and brine and dried over sodium sulfate. Distillation affords 107 g. (80%) of 1-acetoxy-1-ethynylcyclohexane, b.p. 95°–97°/15 mm.

Step 2. Preparation of 1-Acetoxy-1-(3-diethylamino-1-propynyl)cyclohexane

A mixture of 1-acetoxy-1-ethynylcyclohexane (64.00 g., 0.385 mole), diethylamine (30.95 g., 0.424 mole), paraformaldehyde (15.00 g., 0.500 mole), cuprous chloride (1.5 g.) and dioxane (60 ml.) is stirred well. An exothermic reaction gradually results which may require external cooling to prevent spillage. After this initial reaction, the mixture is heated on a steam bath for 1.5 hours.

The cooled reaction mixture is treated with ether and the product is extracted into ice-cold 5% concentrated hydrochloric acid. This cold aqueous acidic solution is then basified with ice-cold 10% sodium hydroxide. The oily amine is extracted with ether and the combined extracts are washed with saturated sodium chloride solution and then dried over anhydrous sodium sulfate. The solvent is removed under vacuum and the residual oil is distilled to give 72.7 g. (75%) of light yellow oil, b.p. 113°–115°/0.15 mm.; pmr $CDCl_3$ S 1.07 (6H,t), 2.02 (3H,s $CH_3COO$), 2.60 (4H,q $CH_3CH_2N$), 3.52 (2H,s $CH_2C\equiv$ :

Step 3. Preparation of 1-Acetoxy-1-(3-bromo-1-propynyl) cyclohexane

Cyanogen bromide (31.8 g., 0.3 mole) is added to a solution of 1-acetoxy-1-(3-diethylamino-1-propynyl)-cyclohexane (61 g., 0.24 mole) and the resulting solution is allowed to stand at 25°–27° C. for 18 hours. The ether solution is washed with 5% hydrochloric acid solution, water and brine and dried over sodium sulfate. The ether is evaporated and the residual oil distilled. There is obtained 34.8 g. (55%) of 1-acetoxy-1-(3-bromo-1-propynyl)-cyclohexane, a slightly yellowish oil, b.p. 114°–120°/0.2 mm.

Q. Preparation of
1-Acetoxy-1-(3-bromo-1-propynyl)-cyclooctane

By use of the procedures described in Example P but starting with 1-ethynyl-cyclooctan-1-ol in Step 1 instead of 1-ethynylcyclohexan-1-ol, there are obtained successively: Step 1, 1-acetoxy-1-ethynylcyclooctane; Step 2, 1-acetoxy-1-(3-diethylamino-1-propynyl)cyclooctane; Step 3, 1-acetoxy-1-(3-bromo-1-propynyl)-cyclooctane.

Preparation of 1-Chloro-4-acetoxy-4-methylnonane

The Grignard reagent prepared from iodomethane (14.2 g., 0.1 mole) and magnesium (2.4 g., 0.1 mole in ether solution is added, dropwise to an ether solution of 1-chloro-4-nonanone (Example A, Step 1) (17.6 g., 0.1 mole). The reaction is refluxed gently for three hours then cooled and poured carefully into ice water (300 ml.). The ether layer is separated, washed with brine, and dried over sodium sulfate. Removal of the ether in vacuo gives 1-chloro-4-hydroxy-4-methylnonane as an oil. The tertiary alcohol is dissolved in pyridine and treated with one molar equivalent of acetic anhydride at 60°–80° for 8–16 hours to give 1-chloro-4-acetoxy-4-methylnonane as a colorless oil.

EXAMPLE 1

Preparation of
7-[1-(4-Hydroxynonyl)ureido]heptanoic acid

Step A. Preparation of Ethyl 7-[N-(4-acetoxynonyl)-cyanamido]-heptanoate

Sodium hydride (57%, in mineral oil) (0.48 g., 0.01 mole) is washed twice with benzene then suspended in benzene (50 ml.) and dimethylformamide (50 ml.). Ethyl 7-cyanamidoheptanoate (1.98 g. 0.01 mole) (Example N, Step 2) is added and the suspension heated on the steam bath for 15 minutes. The reaction mixture is cooled to room temperature, 1-chloro-4-acetoxynonane (2.6 g., 0.01 mole) (Example A, Step 3) is added and then the reaction is heated on the steam bath for 2 hours then stirred 18 hours at room temperature. The reaction is poured into water (300 ml.) and extracted with benzene (3 × 100 ml.). The benzene is washed with brine then dried over sodium sulfate. Removal of the solvent yields an oil which is purified by silica gel chromatography, elution solvent 3% methanol in chloroform, evaporation of the appropriate fraction affords ethyl 7-[N-(4-acetoxynonyl) cyanamido]-heptanoate. The yield is 3.2 g. (83%).

Anal. calcd. for $C_{21}H_{38}N_2O_4$: C, 65.96; H, 9.96; N, 7.32. Found: C, 65.53; H, 10.08; N, 6.94.

Step B. Preparation of 7-[N-(4-Hydroxynonyl)-cyanamido]-heptanoic acid

To a solution of ethyl 7-[N-(4-acetoxynonyl)-cyanamido]-heptanoate (3.6 g., 0.01 mole) in ethanol (40 ml.) is added a water (20 ml.) solution of sodium hydroxide (1.4 g., 0.0035 mole). The reaction is stirred at room temperature for 20 hours, water (100 ml. is added, the solution is acidified (dil. HCl), and extracted with ethyl acetate (3 × 75 ml.). The organic layer is washed with brine, dried over sodium sulfate, then evaporated in vacuo to an oil. The oil is taken up in water (100 ml.) by the careful addition of 10% sodium hydroxide. The basic solution is extracted with ether (2 × 25 ml.) then reacidified with hydrochloric acid (dil.). The oil that separates is taken up in ethyl acetate, the extract is dried over sodium sulfate then concentrated in vacuo to yield the subject compound as a residual oil. The yield is 1.5 g. (48%) of 7-[N-(4-hydroxynonyl)cyanamido]heptanoic acid which exists as the hemihydrate.

Anal. calcd. for $C_{17}H_{32}N_2O_3 \cdot 1/2H_2O$: C, 63.51; H, 10.35; N, 8.71. Found: C, 63.48; H, 10.25; N, 8.35.

Step C. Preparation of 7-[1-(4-Hydroxynonyl)ureido]heptanoic acid

To a solution of sodium hydroxide (0.4 g., excess) in water (50 ml.) and ethanol (50 ml.) is added 7-[N-(4-hydroxynonyl)cyanamido]heptanoic acid (1.5 g., 0.005 mole). The clear solution that is obtained is treated with 30% hydrogen peroxide (1.25 ml., excess). At the end of two hours the reaction mixture is poured into water (150 ml.), acidified with hydrochloric acid (dil.) and extracted with methylene chloride (3 × 75 ml.). The organic layer is washed with brine then dried over sodium sulfate. Evaporation of the solvent affords an oil which becomes solid on standing. The solid is crystallized from butyl chloride to give 7-[1-(4-hydroxynonyl)ureido]heptanoic acid. The yield is 1.4 g. (85%) of natural melting at 75°–76° C.

Anal. calcd. for $C_{17}H_{34}N_2O_4$: C, 61.78; H, 10.37; N, 8.48. Found: C, 62.09; H, 10.69; N, 8.43.

EXAMPLE 2

Preparation of
7-[1-(4-Hydroxy-(E)-2-nonenyl)ureido]-heptanoic acid

The synthesis of this compound is carried out as described in Example 1 except that, in Step A, the 1-chloro-4-acetoxynonane is replaced by an equimolar amount of 1-bromo-4-acetoxy-2-nonane (Example H). The product of Step A is thus ethyl 7-[N-(4-acetoxy-(E)-2-nonenyl)cyanamido]heptanoate.

Anal. calcd. for $C_{21}H_{36}N_2O_4$: C, 66.28; H, 9.45; N, 7.36. Found: C, 65.95; H, 9.45; N, 7.23.

The product of Step G is 7-[N-(4-hydroxy-(E)-2-nonenyl)cyanamido]-heptanoic acid and the product of Step C is 7-[1-(4-hydroxy-(E)-2-nonenyl)ureido]-heptanoic acid. This product is in the form of the hydrate.

Anal. calcd. for $C_{17}H_{32}N_2O_4H_2O$: C, 58.93; H, 9.89; N, 8.07. Found: C, 59.04; H, 9.84; N, 7.96.

Preparation of
7-[1-(4-(4-Hydroxynonyl)thioureido]heptanoic acid

Step A. 7-[1-(4-hydroxynonyl-thioureido]heptanoic acid

A solution of 7-[N-(4-hydroxynonyl)cyanamido]-heptanoic acid (4.2 g., 0.0134 mole) (Example 1, Step B) in thiolacetic acid, (15 ml.), in a vicor flask is irradiated using an ultraviolet lamp for 2.5 hours then allowed to stand overnight. The solvent is removed in vacuo and the resulting oil is dissolved in ammonium hydroxide (150 ml.). This solution is stirred at room temperature for 48 hours, cooled in ice, then acidified with 6N hydrochloric acid. The oil that separates is extracted into ethyl acetate. The acetate layer is dried over sodium sulfate then concentrated in vacuo to an oil that is further purified by silica gel chromatography. The product is eluted from the column with 6% methanol, chloroform mixture and evaporation of the appropriate fractions yield 7-[1-4-(hydroxynonyl)-thioureido]heptanoic acid as a viscous oil. The yield is 3.2 g. (69%).

Anal. calcd. for $C_{17}H_{34}N_2O_3S$: C, 58.92; H, 9.89; N, 8.08. Found: C, 58.95; H, 10.04; N, 7.94.

EXAMPLE 4

Preparation of
7-[1-(4-Hydroxy-2-nonynyl)ureido]heptanoic acid

The synthesis of this compound is carried out as described in Example 1 except that, in Step A, the 1-chloro-4-acetoxynonane is replaced by an equimolar amount of 1-bromo-4-acetoxy-2-nonyne (Example I, Step 3). The product of Step A is thus ethyl 7-[N-(4-acetoxy-2-nonynyl)cyanamido]heptanoate. The subsequent steps yield 7-[N-(4-hydroxy-2-nonynyl)-cynamido]heptanoic acid (B), and 7-[1-(4-hydroxy-2-nonynyl)ureido]heptanoic acid (C).

EXAMPLE 5

Preparation of
7-[1-(4(R)-Hydroxynonyl)ureido]heptanoic acid

The synthesis of this compound is carried out as described in Example 1 except that, in Step A, the 1-chloro-4-acetoxynonane is replaced by an equimolar amount of 1-bromo-4(R)-acetoxy-2-nonyne (Example J). The product of Step A is thus ethyl 7-[N-(4(R)-acetoxy-2-nonynyl)cyanamido]-heptanoate. The subsequent steps yield 7-[N-(4-(R)-hydroxy-2-nonynyl)-cyanamido]heptanoic acid (B), and 7-[1-(4(R)-hydroxy-2-nonynyl)ureido]heptanoic acid (C). The product of Step C is hydrogenated over a platinum on charcoal catalyst to afford 7-[1-(4(R)-hydroxynonyl)ureido]heptanoic acid.

EXAMPLE 6

Preparation of
7-[1-(4(S)-Hydroxynonyl)ureido]heptanoic acid

The synthesis of this compound is carried out as described in Example 1 except that, in Step a, the 1-chloro-4-acetoxynonane is replaced by an equimolar amount of 1-bromo-4(S)-acetoxy-2-nonyne (Example K). The product of Step A is thus ethyl 7-[N-(4(S)-acetoxy-2-nonynyl)cyanamido]heptanoate. The subsequent steps yield 7-[N-(4(S)-hydroxy-2-nonynyl)-cyanamido]heptanoic acid (B) and 7-[1-(4(S)-hydroxy-2-nonynyl)ureido]heptanoic acid (C). The product of Step C is hydrogenated over a platinum on charcoal catalyst to afford 7-[1-(4(S)-hydroxy-nonyl)ureido]heptanoic acid.

EXAMPLE 7

Preparation of
7-[1-(4-Hydroxynonyl)ureido]-2-methylheptanoic acid

Step A. Preparation of Ethyl 7-[N-(4-acetoxynonyl)-cyanamido]-2-methylheptanoate A stirred suspension of sodium hydride (57% in mineral oil) (5.0 g., excess) in a solvent mixture of benzene (75 ml.) and dimethylformide (75 ml.) is treated, over 30 minutes, with 4-acetoxynonylcyanamide (22.6 g., 0.1 mole) (Example O, Step 5) dissolved in benzene (20 ml.). Stirring is continued for one hour. Then, ethyl 7-bromo-2-methylheptanoate (Example L, Step 4) (25.3 g., 0.1 mole) is added dropwise, and the reaction is heated on the steam bath for 3.5 hours. The cooled reaction is poured into water (400 ml.) and extracted with ethyl acetate (2 × 200 ml.). The organic fractions are combined, washed with brine, then dried over sodium sulfate. The solvent is removed in vacuo to give ethyl 7-[N-(4-acetoxynonyl)cyanamido]-2-methylheptanoate as a pale yellow liquid.

Step B. Preparation of 7-[N-(4-hydroxynonyl)-cyanamido]-2-methylheptanoic acid

To a solution of ethyl 7-[N-(4-acetoxynonyl)-cyanamido]-2-methylheptanoate (7.6 g., 0.02 mole) in ethanol (50 ml.) is added a solution of sodium hydroxide (1.6 g., 0.04 mole) in water (15 ml.) and the reaction is stirred at ambient temperature for 20 hours. Then most of the ethanol is removed in vacuo and the residue taken up in water (150 ml.). The solution is extracted once with ether then acidified with hydrochloric acid (dil.). The oil that separates is extracted into ether, the ether is washed with brine, dried over sodium sulfate, then removed under vacuum to give 7-[N-(4-hydroxynonyl)cyanamido]-2-methylheptanoic acid as a yellow oil.

Step C. Preparation of 7-[1-(4-hydroxynonyl)ureido]-2-methylheptanoic acid

To a solution of sodium hydroxide (0.4 g., excess) in water (50 ml.) and ethanol (50 ml.) is added 7-[N-(4-hydroxynonyl)-cyanamido]-2-methylheptanoic acid (1.5 g., 0.005 mole). The clear solution that is obtained is treated with 30% hydrogen peroxide (1.25 ml., excess). After two hours the reaction is poured into water (125 ml.), acidified with 5% hydrochloric acid and extracted with ethyl acetate (3 × 75 ml.). The organic phase is washed with brine, then dried over sodium sulfate. Evaporation of the solvent yields 7-[1-(4-hydroxynonyl)ureido]-2-methyl-heptanoic acid as a viscous oil.

EXAMPLE 8

Preparation of
7-[1-(4-Hydroxynonyl)ureido]-2,2-dimethylheptanoic acid

The synthesis of this compound is carried out as described in Example 7 except that, in Step A, the ethyl 7-bromo-2-methylheptanoate is replaced by an equimolar amount of methyl 2,2-dimethyl-7-iodoheptanoate. The product of Step A is thus methyl 7-[N-(4-acetoxynonyl)cyanamido]-2,2-dimethylheptanoate. The subsequent steps yield 7-[N-(4-hydroxynonyl)cyanamido]-2,2-dimethylheptanoic acid (B) and 7-[1-(4-hydroxynonyl)ureido]-2,2-dimethylheptanoic acid (C).

EXAMPLE 9

Preparation of
7-[1-(4-Hydroxynonyl)ureido]-3-methylheptanoic acid

The synthesis of this compound is carried out as described in Example 7 except that, in Step A, the ethyl 7-bromo-2-methylheptanoate is replaced by an equimolar amount of methyl 3-methyl-7-iodoheptanoate. The product of Step A is thus methyl 7-[N-(4-acetoxynonyl)cyanamido]-3-methylheptanoate. The subsequent steps yield 7-[N-(4-hydroxynonyl)cyanamido]-3-methylheptanoic acid (B) and 7-[1-(4-hydroxynonyl)ureido]-2-methylheptanoic acid (C).

EXAMPLE 10

Preparation of
7-[1-(4-Hydroxynonyl)ureido]-3,3-dimethylheptanoic acid

The synthesis of this compound is carried out as described in Example 7 except that, in Step A, the ethyl 7-bromo-2-methylhaptanoate is replaced by an equimolar amount of methyl 3,3-dimethyl-7-iodoheptanoate. The product of Step A is thus methyl 7-[N-(4-acetoxynonylcyanamido]-3,3-dimethylheptanoate. The subsequent steps yield 7[N-(4-hydroxynonyl)cyanamido]-3,3-dimethylheptanoic acid (B) and 7-[1-(4-hydroxynonyl)ureido]-3,3-dimethylheptanoic acid (C).

EXAMPLE 11

Preparation of
4-[1-(4-Hydroxynonyl)thioureido]butoxy-acetic acid

The synthesis of this compound initially is carried out as described in Example 7 except that, in Step A, the ethyl 7-bromo-2-methylheptanoate is replaced by an equimolar amount of ethyl 4-bromobutoxyacetate (Example M). The product of Step A is thus ethyl 4-[N-(4-acetoxynonyl)cyanamido]butoxyacetate. The product of the hydrolysis (Step B) is thus 4-[N-(4-hydroxynonyl)cyanamido]butoxyacetic acid. This product is then treated as described in Example 3, Step A, to yield the subject compound 4-[1-(4-hydroxynonyl)thioureido]butoxyacetic acid.

EXAMPLE 12

Preparation of
7-[1-(4-Hydroxy-8-methylnonyl)thioureido]heptanoic acid

The synthesis of this compound is carried out initially as described in Example 1 except that, in the 1-chloro-4-acetoxynonane is replaced by an equimolar amount of 1-chloro-4-acetoxy-8-methylnonane (Example B, Step 3). The product of Step A is thus ethyl 7-[N-(4-acetoxy-8-methylnonyl)cyanamido]heptanoate. The hydrolysis (Step B) affords 7-[N-(4-hydroxy-8-methylnonyl)cyanamido]-heptanoic acid. This product is then treated as described in Example 3, Step A, to yield the subject compound 7-[N-(4-hydroxy-8-methylnonyl)thioureido]heptanoic acid.

EXAMPLE 13

Preparation of
7-[1-(4-Hydroxyundecyl)thioureido]heptanoic acid

The synthesis of this compound, initially, is carried out as described in Example 1 except that, in Step A, the 1-chloro-4-acetoxynonane is replaced by an equimolar amount of 1-chloro-4-acetoxyundecane (Example C, Step 3). The product of Step A is thus ethyl 7-[N-(4-acetoxyundecyl)cyanamido]heptanoate. The subsequent steps yield 7-[N-(4-hydroxyundecyl)cyanamido]heptanoic acid (B). This product then is treated as described in Example 3, Step A, to yield the subject compound 7-[1-(4-hydroxyundecyl)thioreido]-heptanoic acid.

EXAMPLE 14

Preparation of
7-[1-(4-Hydroxy-8,8-dimethylnonyl)ureido]heptanoic acid

The synthesis of this compound is carried out as described in Example 1 except that, in Step A, the 1-chloro-4-acetoxynonane is replaced by an equimolar amount of 1-chloro-4-acetoxy-8,8-dimethylnonane (Example D). The product of Step A is thus ethyl 7-[N-(4-acetoxy-8,8-dimethylnonyl)cyanamido]heptanoate. The subsequent steps yield 7-[N-(4-hydroxy-8,8-dimethylnonyl)cyanamido]-heptanoic acid (B) and 7-[1-(4-hydroxy-8,8-dimethylnonyl)ureido]heptanoic acid (C).

EXAMPLE 15

Preparation of
7-[1-(4-Hydroxy-9,9,9-trifluorononyl)ureido]heptanoic acid

The synthesis of this compound is carried out as described in Example 1 except that, in Step A, the 1-chloro-4-acetoxynonane is replaced by an equimolar amount of 1-chloro-4-acetoxy-9,9,9trifluorononane (Example E). The product of Step A is thus ethyl 7-[N-(4-acetoxy-9,9,9-trifluorononyl)cyanamido]heptanoate. The subsequent steps yield 7-[N-(4-hydroxy-9,9,9-trifluorononyl)cyanamido]heptanoic acid (B) and 7-[1-(4-hydroxy-9,9,9-trifluorononyl)-ureido]heptanoic acid (C).

EXAMPLE 16

Preparation of
7-[1-(4-Hydroxy-8-nonenyl)ureido]heptanoic acid

The synthesis of this compound is carried out as described in Example 1 except that, in Step A, the 1-chloro-4-acetoxynonane is replaced by an equimolar amount of 1-chloro-4-aceotoxy-8nonane. The product of Step A is thus ethyl 7-[N-(4-acetoxy-8-nonenyl)-cyanamido]heptanoate. The subsequent steps yield 7-[N-(4-hydroxy-8-nonenyl)cyanamido]heptanoic acid (B) and 7-[1-(4-hydroxy-8-nonenyl)ureido]heptanoic acid (C).

EXAMPLE 17

Preparation of
7-[1-(4-Hydroxy-5,5-dimethylnonyl)ureido]heptanoic acid

The synthesis of this compound is carried out as described in Example 1 except that, in Step A, the 1-chloro-4-acetoxynonane is replaced by an equimolar amount of 1-chloro-4-acetoxy-5,5-dimethylnonane (Example G). The product of Step A is thus ethyl 7-[N-(4-acetoxy-5,5-dimethylnonyl)cyanamido]heptanoate. The subsequent steps yield 7-[N-(4-hydroxy-5,5-dimethylnonyl)cyanamido]heptanoic acid (B) and 7-[1-(4-hydroxy-5,5-dimethylnonyl)ureido]heptanoic acid (C).

EXAMPLE 18

Preparation of
7-[1-(4-Hydroxy-4-methylnonyl)ureido]heptanoic acid

The synthesis of this compound is carried out as described in Example 1 except that, in Step A, the 1-chloro-4-acetoxynonane is replaced by an equimolar amount of 1-chloro-4-acetoxy-4-methylnonane (Example R). The product of Step A is thus ethyl 7-[N-(4-acetoxy-4-methylnonyl)-cyanamido]heptanoate. The subsequent steps yield 7-[N-(4-hydroxy-4-methylnonyl)cyanamido]heptanoic acid (B) and 7-[1-(4-hydroxy-4-methylnonyl)ureido]heptanoic acid (C).

Anal. calcd. for $C_{18}H_{36}N_2O_4$: C, 62.77; H, 10.53; N, 8.13. Found: C, 62.51; H, 11.08 N, 7.75.

EXAMPLE 19

Preparation of
7-{1-[3-(1-Hydroxycyclohexyl)-2-propyn-1-yl]ureido}heptanoic acid The synthesis of this compound is carried out as described in Example 1 except that, in Step A, the 1-chloro-4-acetoxynonane is replaced by an equimolar amount of 1-acetoxy-1-(3-bromo-1-propynyl)cyclohexane (Example P). The product of Step A is thus ethyl 7-{N-[3-(1-acetoxycyclohexyl)-2-propyn-1-yl]cyanamido}heptanoate. The subsequent steps yield 7-{N-[3-(1-hydroxycyclohexyl)-2-propyn-1-yl]-cyanamido}heptanoic acid (B) and 7-{1-[3-(1-hydroxycyclohexyl)-2-propyn-1-yl]ureido}heptanoic acid (C).

EXAMPLE 20

Preparation of
7-{1-[3-(1-Hydroxycyclohexyl)propyl]ureido}-heptanoic acid

Hydrogenation of 7-{1-[3-(1-hydroxycyclohexyl)-2-propyn-1-yl]ureido}heptanoic acid (Example 19) over a platinum on charcoal catalyst affords 7-{1-[3-(1-hydroxycyclohexyl)propyl]ureido}heptanoic acid as a pale yellow oil.

EXAMPLE 21

Preparation of
7-{1-[3-(1-Hydroxycyclooctyl)-2-propyn-1-yl]ureido}heptanoic acid The synthesis of this compound is carried out as described in Example 1 except that, in Step A, the 1-chloro-4-acetoxynonane is replaced by a equimolar amount of -1-acetoxy-1-(3-bromo-1-propynyl)cyclooctane (Example Q). The product of Step A is thus ethyl 7-{N-[3-(1-acetoxycyclooctyl)-2-propyn-1-yl]cyanamido}heptanoate. The subsequent steps yield 7-{N-[3-(1-hydroxycyclooctyl)-2-propyn-1-yl]cyanamido}heptanoic acid (B) and 7-{1-[3-(1-hydroxycyclooctyl)-2-propyn-1-yl]ureido}heptanoic acid (C).

EXAMPLE 22

Preparation of
7-{1-[3-(1-Hydroxycyclooctyl)propyl]ureido}heptanoic acid

Hydrogenation of 7-{1-[3-(1-hydroxycyclooctyl)-2-propyn-1-yl]ureido}heptanoic acid (Example 21) over a platinum on charcoal catalyst affords 7-{1-[3-(1-hydroxycyclooctyl)propyl]ureido}heptanoic acid.

EXAMPLE 23

Preparation of methyl
7-[1-(4-Hydroxynonyl)thioureido]heptanoate

A solution of diazomethane (approx. 2.5 g., 0.06 mole) in ether (100 ml.) is mixed with a solution of 7-[1-(4-hydroxynonyl)thioureido]heptanoic acid (10.3 g., 0.03 mole) (Example 3) in ether (50 ml.). The resulting solution is allowed to stand at room temperature for 4 hours. Then acetic acid is added to destroy the excess diazomethane and the solution is washed with dilute sodium bicarbonate solution, brine, then dried over sodium sulfate. Evaporation of volatile materials at reduced pressure yields methyl 7-[1-(4-hydroxynonyl)thioureido]heptanoate as a viscous oil.

EXAMPLE 24

Preparation of Decyl
7-[1-(Hydroxynonyl)ureido]heptanoate

Using the method of Example 23 but substituting an ether solution of 1-diazodecane for the ether solution of diazomethane and 7-[1-(4-hydroxynonyl)ureido]-heptanoic acid for 7-[1-(4-hydroxynonyl)thioureido]-heptanoic acid, there is obtained decyl 7-[1-(4-hydroxynonyl)ureido]-heptanoate as a viscous oil.

EXAMPLE 25

Preparation of
N-[(2-Dimethylamino)ethyl]-7-[1-(4-hydroxynonyl)ureido]heptanamide A solution of 7-[1-(4-hydroxynonyl)ureido]-heptanoic acid (3.3 g., 10 mm.) (Example 1, Step C), triethylamine (1.74 ml., 12.5 mm.) and distilled water (18 ml.) in acetonitrile (100 ml.) is treated with N-t-butyl-5-methyl-isoxazolium perchlorate (3.0 g., 12.5 mm.). The resulting solution is evaporated in vacuo at 20°–25° C. over 4 hours providing a tacky residue which is triturated with water (150 ml.) at 0°–5° C. for 15 minutes. After decanting the aqueous phase, the oily residue is dissolved in a 1: mixture of benzene-ether (200 ml.). The organic extract is dried over sodium sulfate, then evaporated in vacuo providing the desired "active ester".

A solution of 2-dimethylaminothylamine (0.88 g., 10 mm.) in acetonitrile (25 ml.) is added to a solution of the active ester in acetonitrile (25 ml.) and the solution is stirred at 25° C. for 17 hours. The solvent is removed in vacuo, the residual oil is partitioned between ether (200 ml.) and water (200 ml.). The ether layer is extracted with 5% hydrochloric acid (2 × 50 ml.). The aqueous phase is made basic with aqueous sodium carbonate then extracted with ether. The ether extract is washed with brine (100 ml.), dried over sodium sulfate, evaporated in vacuo leaving the N-[2-(dimethylamino)ethyl]-7-[1-(4-hydroxynonyl)ureido]heptanamide as a viscous oil.

EXAMPLE 26

Preparation of 7-[1-(4-Hydroxynonyl)ureido]heptanamide

Using the method of Example 25 but substituting an acetonitrile solution of ammonia for the acetonitrile solution of 2-dimethylaminoethylamine, there is obtained 7-[1-(4-hydroxynonyl)ureido]heptanamide.

EXAMPLE 27

Preparation of 7-[1-(4-Acetoxynonyl)ureido]heptanoic acid

A mixture of 7-[1-(4hydroxynonyl)ureido]heptanoic acid (9.9 g., 0.03 mole) (Example 1, Step C) and acetic anhydride (6.1 g., 0.06 mole) is heated at 60° C. for 18 hours. The mixture is cooled and taken up in 80 ml. of ethyl ether. The solution is extracted with an ice-cold solution of 8 g. of sodium hydroxide in 150 ml. of water. The basis solution is separated and acidified with concentrated hydrochloric acid. The oil that separates is extracted into ether, washed with water and dried over sodium sulfate. The ether is evaporated and the residual oil is purified by chromatography on silica gel using 2% methanol in chloroform as the eluting solvent. Thus there is obtained 7-[1-(4-acetoxynonyl)ureido]-heptanoic acid as a yellow oil.

By substituting for the acetic anhydride used in Example 27, an equivalent amount of propionic anhydride, butyric anhydride, isobutyric anhydride, valeric anhydride, or pivalic anhydride and conducting the reaction as described in Example 27, there is obtained 7-[1-(4-propionyloxynonyl)-ureido]heptanoic acid, 7-]1-(4-butyryloxynonyl) ureido]-heptanoic acid, 7-[1-(4-isobutyryloxynonyl)ureido]heptanoic acid, 7-[1-(4-valeryloxynonyl)ureido]heptanoic acid, and 7-[1-(4-pivaloyloxynonyl)ureido]heptanoic acid, respectively.

EXAMPLE 28

Capsule Formulation

| | |
|---|---|
| 7-[1-(4-hydroxynonyl)ureido] heptanoic acid | 50 gm. |
| Stearic Acid (U.S.P. triple pressure) | 125 gm. |
| Pluronic F-68 | 7.5 gm. |
| Corn starch | 125 gm. |

The stearic acid and pluronic are united in a vessel and melted using a water bath at 60°–65° C. The heating is discontinued and the 7-[1-(4-hydroxynonyl)ureido]-heptanoic acid is dispersed into the mixture and the corn starch is added with stirring which is continued until the mixture cools to ambient temperature. The mixture is reduced to granules by screening and placed in a number 0 hard gelatin containing 307.5 mg. of total solids and 50 mg. of 7-[1-(4-hydroxynonyl)ureido]heptanoic acid per capsule.

EXAMPLE 29

Parenteral Formulation of a Multidose Solution for Intramuscular and Intravenous Use

| | |
|---|---|
| 7-[1-(4-hydroxynonyl)thioureido] heptanoic acid | 1 gm. |
| Tris(hydroxymethyl)amino-methane (Reagent Grade Tham) | q.s. to adjust solution to pH 7.4 |
| Sodium chloride (U.S.P.) | q.s. to yield isotonic solution |
| Methylparaben | 10 mg. |
| Propylparaben | 1 mg. |
| Distilled Water (pyrogen-free) | q.s. to 10 ml. |

The 7-[1-(4-hydroxynonyl)thioureido]heptanoic acid suspended in about 6 ml. of the water is treated with tris(hydroxymethyl)aminomethane with stirring until the pH reaches 7.4. The methylparaben and propylparaben are added with stirring and sufficient sodium chloride added to produce an isotonic solution. After water is added to bring the final volume to 10 ml., the solution is sterilized by membrane filtration and placed in a vial by an aseptic technique. The solution contains the Tham salt of 7-[1-(4-hydroxynonyl)thioureido]heptanoic acid equivalent to 100 mg./ml. of the free acid.

EXAMPLE 30

Preparation of Suppositories

| | |
|---|---|
| 7-[1-(4-hydroxy-4-methylnonyl)ureido] heptanoic acid | 200 gm. |
| Butylated hydroxyanisole | 82 mg. |
| Butylated hydroxytoluene | 82 mg. |
| Ethylenediamine tetraacetic acid | 163 mg. |
| Glycerine, U.S.P. | 128 gm. |
| Sodium chloride, microfine | 52.5 gm. |
| Polyethylene glycol 6000 | 128 gm. |
| Polyethylene glycol 4000 | 1269 gm. |

The polyethylene glycol 4000 and polyethylene glycol 6000 were placed in a vessel surrounded by a water bath at such a temperature required to maintain the melted contents at 60°–65° C. To the melt is added the butylated hydroxyanisole and butylated hydroxytoluene with stirring. Then the ethylenediamine tetraacetic acid and microfine sodium chloride are added to and dispersed in the mixture. The 7-[1-(4-hydroxy-4-methylnonyl)ureido]heptanoic acid is then added and dispersed into the mixture. Finally, the temperature is lowered to 55°–60° C. and the glycerine added and dispersed.

While maintaining the temperature of 55°–60° C. and continuous mixing, the melt is dispersed into plastic suppository cavities of a conventional suppository cold-molding device. The suppositories thus prepared contain a total of 1.7778 gm. of contents of which 200 mg. are 7-[1-(4-hydroxy-4methylnonyl)ureido]heptanoic acid.

What is claimed is:

1. The compound having the following formula:

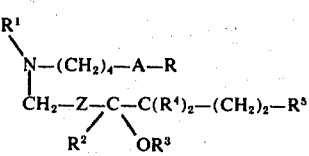

wherein R is carboxy, a carboxy salt, said salt being formed from a pharmaceutically acceptable cation selected from the group of metals and amines, or derivatized carboxy having the formula

—COOY wherein
Y is alkyl having 1–10 carbon atoms;
A is ethylene, trimethylene, α-methylethylene, β-methylethylene, α,α-dimethylethylene, or β,β-dimethylethylene;
$R^1$ is carbamoyl or thiocarbamoyl;
Z is methylene, ethylene, trimethylene, tetramethylene, vinylene, or ethynylene;
$R^2$ is independently hydrogen or methyl;
$R^3$ is hydrogen or loweralkanoyl;
$R^4$ is selected independently from the group consisting of hydrogen and methyl;
$R^5$ is selected from the group consisting of hydrogen, lower alkyl of 1–4 carbon atoms, vinyl and 2,2,2-trifluoroethyl.

2. The compound of claim 1 which has the formula

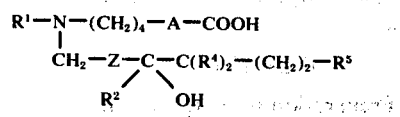

wherein
$R^1$ is carbamoyl or thiocarbamoyl;
$R^2$ is hydrogen or methyl;
A is ethylene, trimethylene, α-methylethylene, β-methylethylene, α,α-dimethylethylene, or β,β-dimethylethylene;
Z is methylene, ethylene, trimethylene or tetramethylene;
$R^4$ is hydrogen or methyl; and
$R^5$ is hydrogen, loweralkyl, vinyl, or 2,2,2-trifluoroethyl.

3. The compound of claim 2 wherein $R^2$ is hydrogen and $R^4$ is methyl.

4. The compound of claim 2 wherein $R^2$ is methyl and $R^4$ is hydrogen.

5. The compound of claim 4 wherein Z is ethylene, $R^1$ is carbamoyl, A is ethylene and $R^5$ is ethyl, which is 7-[1-(4-hydroxy-4-methylnonyl)ureido]heptanoic acid.

6. The compound of claim 2 wherein $R^2$ and $R^4$ are hydrogen.

7. The compound of claim 6 where Z is ethylene.

8. The compound of claim 7 wherein A is α,α-dimethylethylene, $R^1$ is carbamoyl, and $R^5$ is ethyl, which is 7-[1-(4-hydroxynonyl)ureido]-2,2-dimethyl heptanoic acid.

9. The compound of claim 7 wherein A is α-methylethylene, $R^1$ is carbamoyl and $R^5$ is ethyl, which is 7-[1-(4-hydroxynonyl)ureido]-2-methyl heptanoic acid.

10. The compound of claim 7 wherein A is β-methylethylene, $R^1$ is carbamoyl and $R^5$ is ethyl, which is 7-[1-(4-hydroxynonyl)ureido]-3-methyl heptanoic acid.

11. The compound of claim 7 wherein A is β,β-dimethylethylene, $R^1$ is carbamoyl and $R^5$ is ethyl which is 7-[1-(4-hydroxynonyl)ureido]-3,3-dimethyl heptanoic acid.

12. The compound of claim 7 wherein A is ethylene.

13. The compound of claim 12 in which $R^1$ is carbamoyl.

14. The compound of claim 13 wherein $R^5$ is 2,2,2-trifluoroethyl.

15. The compound of claim 13 wherein $R^5$ is t-butyl.

16. The compound of claim 13 wherein $R^5$ is vinyl.

17. The compound of claim 12 in which $R^1$ is thiocarbamoyl.

18. The compound of claim 17 wherein $R^5$ is ethyl, which is 7-[1-(4-hydroxynonyl)thioureido]heptanoic acid.

19. The compound of claim 17 wherein $R^5$ is isopropyl.

20. The compound of claim 17 wherein $R^5$ is n-butyl.

21. The compound of claim 13 wherein $R^5$ is ethyl, which is 7-[1-(4-hydroxynonyl)ureido]heptanoic acid.

22. 7-[1-(4-(R)hydroxynonyl)ureido]heptanoic acid, the compound of claim 21 wherein the carbon atom bearing the hydroxy group is in the R configuration.

23. 7-[1-(4-(S)hydroxynonyl)ureido]heptanoic acid, the compound of claim 21 wherein the carbon atom bearing the hydroxy group is in the S configuration.

24. The compound of claim 1 which has the formula

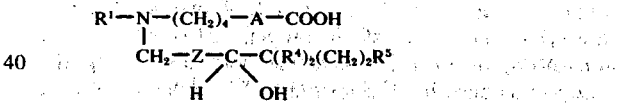

wherein
Z is vinylene or ethynylene;
$R^1$ is carbamoyl or thiocarbamoyl;
A is ethylene, trimethylene, α-methylethylene, β-methylethylene, α,α-dimethylethylene, or β,β-dimethylethylene;
$R^4$ is hydrogen or methyl; and
$R^5$ is hydrogen or loweralkyl of 1 to 4 carbon atoms, vinyl, or 2,2,2-trifluoroethyl.

25. The compound of claim 24 wherein A is ethylene.

26. The compound of claim 25 wherein $R^4$ is hydrogen.

27. The compound of claim 26 wherein Z is vinylene.

28. The compound of claim 27 wherein $R^1$ is carbamoyl, and $R^5$ is ethyl.

29. The compound of claim 26 wherein Z is ethynylene.

30. The compound of claim 29 wherein $R^1$ is carbamoyl, and $R^5$ is ethyl.

* * * * *